(12) United States Patent
Rothschild et al.

(10) Patent No.: US 7,081,335 B2
(45) Date of Patent: Jul. 25, 2006

(54) PROLACTIN RECEPTOR GENE AS A GENETIC MARKER FOR INCREASED LITTER SIZE IN ANIMALS

(75) Inventors: Max F. Rothschild, Ames, IA (US); Amy L. Vincent, Jewell, IA (US); Christopher K. Tuggle, Ames, IA (US); Christy Gladney, Berkeley, CA (US); Alan Mileham, Berkeley, CA (US); Olwen Southwood, Abingdon (GB); Graham Plastow, Cambridge (GB); Carole Sargent, Cambridge (GB)

(73) Assignees: Iowa State University Research Foundation, Inc., Ames, IA (US); PIG Improvement Company UK Limited (GB)

( * ) Notice: Subject to any disclaimer, the term of this patent is extended or adjusted under 35 U.S.C. 154(b) by 632 days.

(21) Appl. No.: 09/900,063

(22) Filed: Jul. 6, 2001

(65) Prior Publication Data

US 2002/0160372 A1     Oct. 31, 2002

Related U.S. Application Data

(63) Continuation-in-part of application No. 09/274,655, filed on Mar. 23, 1999, now abandoned, which is a continuation of application No. 08/812,208, filed on Mar. 6, 1997, now Pat. No. 5,935,784, which is a continuation of application No. 08/742,805, filed on Nov. 1, 1996, now abandoned.

(60) Provisional application No. 60/022,180, filed on Jul. 19, 1996.

(51) Int. Cl.
*C12Q 1/68*   (2006.01)
*C12P 19/34*   (2006.01)

(52) U.S. Cl. .......................................... 435/6; 435/91.2

(58) Field of Classification Search .................... 435/6, 435/91.2; 536/23.1, 24.3
See application file for complete search history.

(56) References Cited

U.S. PATENT DOCUMENTS

| | | | | |
|---|---|---|---|---|
| 5,374,526 A | * | 12/1994 | Rothschild et al. | 435/6 |
| 5,550,024 A | | 8/1996 | Rothschild | 435/6 |
| 5,614,364 A | | 3/1997 | Tuggle | 435/6 |
| 5,935,784 A | | 8/1999 | Rothschild | 435/6 |

FOREIGN PATENT DOCUMENTS

| | | |
|---|---|---|
| WO | WO 96/33288 | 10/1996 |
| WO | WO 96/41892 | 12/1996 |
| WO | WO 98/03682 | 1/1998 |

OTHER PUBLICATIONS

Thisted, R. "What is a P-value" (1998) Http://www.stat.uchicago.edu/ Thisted.*
Martin, E., "Analysis of Association at single nucleotide polymorphisms in the APOE region", *Genomics* 63:7-12 (2000).
Messer, L. et al., "Mapping and investigation of candidate genes for litter size in french white pigs", *Animal Genetics*, 27(2) Dec. 1996 pp. 114 (ABS E056 X_002115295).
Messer, L., et al., "Linkage mapping of the retinol-binding protein 4 (RBP4) gene to porcine chromosome 14", *Mammalian Genome*, 7(5) 1996, p. 396 (XP002115296).
Rothschild, et al., "The estrogen receptor locus is associated with a major gene influencing litter size in pigs", *Proc. Natl. Acad. Sci. USA* 93:201-205 (1996).
Stratagene Catalog, pp. 131 and 161 (1995).
Edery et al., "Identification and sequence analysis of a second form of prolactin receptor by molecular cloning of complementary DNA from rabbit mammary gland", Proc. Natl. Acad. Sci. 89:2112-2116 (1989).
Sommers et al., "Minimal homology requirements for PCR primers", Nucleic Acids Res. 17(16):6749 (1989).

\* cited by examiner

*Primary Examiner*—Jeffrey Fredman
(74) *Attorney, Agent, or Firm*—McKee, Voorhees & Sease, P.L.C.

(57) ABSTRACT

Disclosed herein are genetic markers for animal litter size, methods for identifying such markers, and methods of screening animals to determine those more likely to produce larger litters and preferably selecting those animals for future breeding purposes. The markers are based upon the presence or absence of certain polymorphisms in the prolactin receptor gene.

5 Claims, 5 Drawing Sheets

AAGTCAACAA AGATGGAGCA CTGGCGTTGC TCCCAAAACA GCAGGAGAAC

GGCGACCGGC CGGAGAAGGC TGGCGCCCCT GAAACCAGCA AGGAATACG

CCCAGGTGTC CCGGGTGATG GATAACCACA TCCTGGTGTT AGTGCAGGAT

CCGCGAGCTC GAAACGTGGC TCCGTTTGAA GAACCAACCA AGGAGACCCC

GCCATCCCGG CCGCAGAATC CAGCTGCGAA AGACCTGGCC G/AGCTTCACCA

CGGCCCCGGG CCACTGCAGA CACCCGCTGG GTGGGCTGGA TTACCTCGAT

CCCGCAGGCT TTATGCACTC CTTTCAGTGA GAGCTTGGTT CATGGGATGA

TGGGTTACAA GGTGGGGTTT TTTTCAGGTC GCACTACGTG AAATGCACTC

TACCAGAGAA AGCTCGAAAA TGGGGTTAGA ATGACACTAC *CCAGACTCAC*

*AGTTCACTCC TCTTCATGCT* CCATTTTCAA CCACTTGCCTCTT

G/A=G or A at polymorphic site

*Fig. 1*

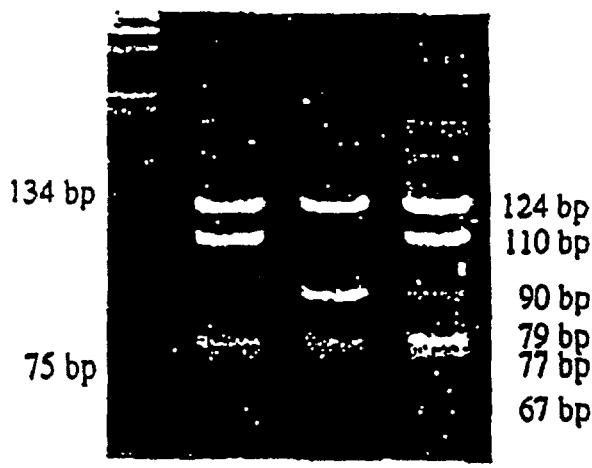

*Fig. 2*

```
  1 GATTATTGTC TGGGCAGTGG ---------- TCTTCTCTGT CTATCNACCC CCCTCCCATT  60
 61 CATGGCTCTC AGGGTATAAT GGCCAAAAAA AAGACAAGAC AAAAATGATG GAAACCTACA 120
121 GATAATTYAA GCACCTCATT TTGCCATTAG CTGCATTAGC CATAAAAAAA A--------- 180
181 -----AAAAA AAAACCTTTT CTCAGTGCTA GAAAAAAACA GAATAGACTC ATTTGAAACT 240
241 GATCTTCTCT CTACCAAAGG GAGTAGCGCA GTTGTGAAAT AGTAAACGTC TGACAAGAAC 300
301 AGCAAATAAT CCCACTAGTA ATTTCAGAAT CCGCCTCCTC AATTAGCCAG AATTCACTGT 360
361 GATGCTGGCC TCTATAATTA TTATTTGTCT TCACCACTGA TTAGTTTCAC ATCATGAAAA 420
421 TTGCATGTCA TTTAGTTTCA CRTAGCCTCA GAACCAACCC TAATTCCTAC CTGCCATATC 480
481 CCTGTAGCAG CTATTCGAAG ATCACAAGGT GGGAACATGT GTYATTTATC TTTTCTCTTA 540
541 CATTATTTTA GAGCATGGTG GCCTGCATCC ---------- GGGCCAAAAA TAAAAGGATT 600
```

*Fig. 5*

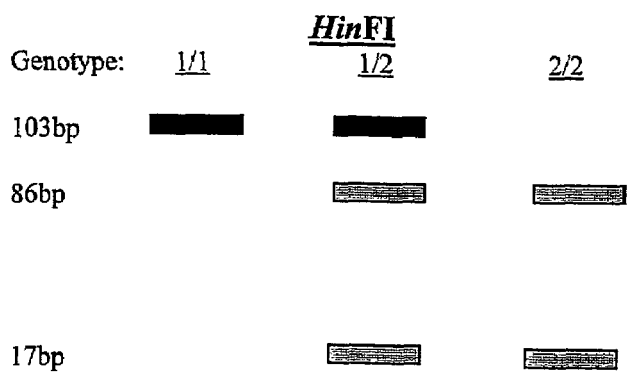

*Fig. 6*

Sequence 5' to 3' for porcine PRLR Sequence

GTACACACAC ACACACACAC ACACACACAC ACACACCACC GTTAAGCTNT CTTTCTGAAT CATGCCNACC
CGAGGGCCAC CCATAGAGGA GTGTGGTGGA GGGTGCCTTG GCACTTCTGA GCCCTGCATC CCTACACCCA
CTAGCCTCAA GATGTCATC CCTGCCCTGG CCCCCACCCA TCTGCTTCTG TCACCAGCAG AATGGTCCAG
TCATTGAGCG GACCTTCATA TTGACTCCAG TGGCTTCTGG CTTTTCTAG GACAGTCACC TCCGGGAAAA
CCTGAGATCT TCAAATGTCG TTCTCCCGAA AAGGAAACAT TCGCCTGCTG GTGGAAGCCG GGGGCGGATG
GAGGACTTCC TACCAACTAG ACGCTGACTT ACCACAAGGA AGGGTAAGCA TTCGCGTGTC TCCCAACAAA
CCACACGAGT GTTCTCTCTC TGTGGGCCAG AGGAACACTG CTTCTGGGTT AGAACTGCCT CGCTTTGGAG
TTCCCGTCAT GGCTCAGTGG TAACGAATC

Human exon 4 gacagttacctcctgg aaaacctgag atctttaaat gtcgttctcc caataaggaa acattcacct
gctggtggag gcctgggaca gatggaggac ttcctaccaa ttattcactg acttaccaca
gggaagg Alignment
        E x o n 4
Hsap    g a c a g t t a c c t c c t g g a a a a c c t g a g a t c t t t a a a t
        G    Q    L    P    P    G    K    P    E    I    F    K pig     ? a c a g t c a c c t c c g g g a a a a c c t g a g a t c t t c a a a t
              S          P                               F Hsap    g t c g t t c t c c c a a t a a g g a a a c a t t c a c c t g c t g g t
        C    R    S    P    N    K    E    T    F    T pig     g t c g t t c t c c c g a a a a g g a a a c a t t c g c c t g c t g g t
                    E                               A Hsap    g g a g g c c t g g g a c a g a t g g a g g a c t t c c t a c c a a t t
          R    P    G    T    D    G    G    L    P    T    N pig     g g a a g c c g g g g g c g g a t g g a g g a c t t c c t a c c a a c t
          K    P        A                             N Hsap    a t t c a c t g a c t t a c c a c a g g g a a g g
        Y    S    L    T    Y    H    R    E    G pig     ? g a c g c t g a c t t a c c a c a a g g a a g g
      **     T                           K

Fig.9

SEQUENCE LISTING

```
<160> NUMBER OF SEQ ID NOS: 18

<210> SEQ ID NO 1
<211> LENGTH: 20
<212> TYPE: DNA
<213> ORGANISM: Porcine

<400> SEQUENCE: 1
cccaaaacag caggagaacg                                              20

<210> SEQ ID NO 2
<211> LENGTH: 20
<212> TYPE: DNA
<213> ORGANISM: Porcine

<400> SEQUENCE: 2
ggcaagtggt tgaaaatgga                                              20

<210> SEQ ID NO 3
<211> LENGTH: 492
<212> TYPE: DNA
<213> ORGANISM: Porcine
<220> FEATURE:
```

```
<221> NAME/KEY: allele
<222> LOCATION: (240)..(240)
<223> OTHER INFORMATION: G/A polymorphic site

<400> SEQUENCE: 3
aagtcaacaa agatggagca ctggcgttgc tcccaaaaca gcaggagaac ggcgaccggc      60
cggagaaggc tggcgcccct gaaaccagca aggaatacgc ccaggtgtcc cgggtgatgg     120
ataaccacat cctggtgtta gtgcaggatc cgcgagctcg aaacgtggct ccgtttgaag     180
aaccaaccaa ggagacccg ccatcccggc cgcagaatcc agctgcgaaa gacctggccg      240
gcttcaccac ggccccggc cactgcagac acccgctggg tgggctggat tacctcgatc      300
ccgcaggctt tatgcactcc tttcagtgag agcttggttc atgggatgat gggttacaag     360
gtggggtttt tttcaggtcg cactacgtga atgcactct accagagaaa gctcgaaaat      420
ggggttagaa tgacactacc cagactcaca gttcactcct cttcatgctc cattttcaac     480
cacttgcctc tt                                                         492

<210> SEQ ID NO 4
<211> LENGTH: 20
<212> TYPE: DNA
<213> ORGANISM: Unknown
<220> FEATURE:
<223> OTHER INFORMATION: Human and rabbit cDNA sequences encoding the
      prolactin receptor were used to design the degenerate primer
<220> FEATURE:
<221> NAME/KEY: misc_difference
<222> LOCATION: (13)..(13)
<223> OTHER INFORMATION: C/T

<400> SEQUENCE: 4
tcacaaggtc aacaaagatg                                                  20

<210> SEQ ID NO 5
<211> LENGTH: 20
<212> TYPE: DNA
<213> ORGANISM: Unknown
<220> FEATURE:
<223> OTHER INFORMATION: Human and rabbit cDNA sequences encoding the
      prolactin receptor were used to design the degenerate primer
<220> FEATURE:
<221> NAME/KEY: misc_difference
<222> LOCATION: (3)..(3)
<223> OTHER INFORMATION: G/A
<220> FEATURE:
<221> NAME/KEY: misc_difference
<222> LOCATION: (9)..(9)
<223> OTHER INFORMATION: G/A
<220> FEATURE:
<221> NAME/KEY: misc_difference
<222> LOCATION: (16)..(16)
<223> OTHER INFORMATION: G/A

<400> SEQUENCE: 5
tggagaaaga ggcaagtggt                                                  20

<210> SEQ ID NO 6
<211> LENGTH: 20
<212> TYPE: DNA
<213> ORGANISM: Porcine

<400> SEQUENCE: 6
cggccgcaga atcctgctgc                                                  20

<210> SEQ ID NO 7
<211> LENGTH: 24
```

```
<212> TYPE: DNA
<213> ORGANISM: Porcine

<400> SEQUENCE: 7
accccacctt gtaacccatc atcc                                          24

<210> SEQ ID NO 8
<211> LENGTH: 18
<212> TYPE: DNA
<213> ORGANISM: Porcine

<400> SEQUENCE: 8
caaggtggga acatgagt                                                 18

<210> SEQ ID NO 9
<211> LENGTH: 20
<212> TYPE: DNA
<213> ORGANISM: Porcine

<400> SEQUENCE: 9 aatccttta tttttggccc                                                20

<210> SEQ ID NO 10
<211> LENGTH: 20
<212> TYPE: DNA
<213> ORGANISM: Porcine

<400> SEQUENCE: 10
gattattgtc tgggcagtgg                                               20

<210> SEQ ID NO 11
<211> LENGTH: 20
<212> TYPE: DNA
<213> ORGANISM: Porcine

<400> SEQUENCE: 11 aatccttta tttttggccc                                                20

<210> SEQ ID NO 12
<211> LENGTH: 20
<212> TYPE: DNA
<213> ORGANISM: Porcine

<400> SEQUENCE: 12
gattattgtc tgggcagtgg                                               20

<210> SEQ ID NO 13
<211> LENGTH: 23
<212> TYPE: DNA
<213> ORGANISM: Porcine

<400> SEQUENCE: 13
ctatttcaca aaaactgcgc tac                                           23

<210> SEQ ID NO 14
<211> LENGTH: 566
<212> TYPE: DNA
<213> ORGANISM: Porcine
<220> FEATURE:
<221> NAME/KEY: misc_feature
<222> LOCATION: (36)..(36)
<223> OTHER INFORMATION: n = unknown at nucleotide position 36

<400> SEQUENCE: 14
```

```
gattattgtc tgggcagtgg tcttctctgt ctatcnaccc ccctcccatt catggctctc      60
agggtataat ggccaaaaaa aagacaagac aaaaatgatg gaaacctaca gataattyaa     120
gcacctcatt ttgccattag ctgcattagc cataaaaaaa aaaaaaaaaa cctttctca      180 gtgctagaaa aaacagaat agactcattt gaaactgatc ttctctctac caaagggagt     240
agcgcagttg tgaaatagta aacgtctgac aagaacagca ataatccca ctagtaattt      300 cagaatccgc ctcctcaatt agccagaatt cactgtgatg ctggcctcta taattattat    360
ttgtcttcac cactgattag tttcacatca tgaaaattgc atgtcattta gtttcacrta    420
gcctcagaac caaccctaat tcctacctgc catatccctg tagcagctat tcgaagatca    480
caaggtggga acatgtgtya tttatctttt ctcttacatt attttagagc atggtggcct    540
gcatccgggc caaaaataaa aggatt                                         566

<210> SEQ ID NO 15
<211> LENGTH: 518
<212> TYPE: DNA
<213> ORGANISM: Porcine
<220> FEATURE:
<221> NAME/KEY: misc_feature
<222> LOCATION: (49)..(49)
<223> OTHER INFORMATION: n = unknown in nucleotide position 49
<220> FEATURE:
<221> NAME/KEY: misc_feature
<222> LOCATION: (67)..(67)
<223> OTHER INFORMATION: n = unknown in nucleotide position 67

<400> SEQUENCE: 15
gtacacacac acacacacac acacacacac acacaccacc gttaagctnt ctttctgaat    60
catgccnacc cgagggccac ccatagagga gtgtggtgga gggtgccttg gcacttctga   120
gccctgcatc cctacaccca ctagcctcaa gatgtcatcc ctgccctggc ccccacccat   180
ctgcttctgt caccagcaga atggtccagt cattgagcgg accttcatat tgactccagt   240
ggcttctggc ttttttctagg acagtcacct ccgggaaaac ctgagatctt caaatgtcgt   300
tctcccgaaa aggaaacatt cgcctgctgg tggaagccgg gggcggatgg aggacttcct   360
accaactaga cgctgactta ccacaaggaa gggtaagcat tcgcgtgtct cccaacaaac   420
cacacgagtg ttctctctct gtgggccaga ggaacactgc ttctgggtta gaactgcctc   480
gctttggagt tcccgtcatg gctcagtggt aacgaatc                            518

<210> SEQ ID NO 16
<211> LENGTH: 133
<212> TYPE: DNA
<213> ORGANISM: Homo sapiens

<400> SEQUENCE: 16
gacagttacc tcctggaaaa cctgagatct ttaaatgtcg ttctcccaat aaggaaacat     60
tcacctgctg gtggaggcct gggacagatg gaggacttcc taccaattat tcactgactt    120
accacaggga agg                                                        133

<210> SEQ ID NO 17
<211> LENGTH: 53
<212> TYPE: PRT
<213> ORGANISM: Homo sapiens

<400> SEQUENCE: 17

Gly Gln Leu Pro Pro Gly Lys Pro Glu Ile Phe Lys Ser Pro Phe Cys
1               5                   10                  15
```

-continued

```
Arg Ser Pro Asn Lys Glu Thr Phe Thr Glu Ala Arg Pro Gly Thr Asp
            20                  25                  30

Gly Gly Leu Pro Thr Asn Lys Pro Ala Asn Tyr Ser Leu Thr Tyr His
        35                  40                  45

Arg Glu Gly Thr Lys
    50

<210> SEQ ID NO 18
<211> LENGTH: 132
<212> TYPE: DNA
<213> ORGANISM: Porcine

<400> SEQUENCE: 18
acagtcacct ccgggaaaac ctgagatctt caaatgtcgt tctcccgaaa aggaaacatt      60
cgcctgctgg tggaagccgg gggcggatgg aggacttcct accaactaga cgctgactta    120
ccacaaggaa gg                                                        132
```

PROLACTIN RECEPTOR GENE AS A GENETIC MARKER FOR INCREASED LITTER SIZE IN ANIMALS

CROSS REFERENCE TO RELATED APPLICATION

This application is a continuation-in-part of commonly owned U.S. patent application Ser. No. 09/274,655 filed Mar. 23, 1999, which is a continuation of commonly owned U.S. patent application Ser. No. 08/812,208 filed Mar. 6, 1997 which is a continuation of commonly owned U.S. patent application Ser. No. 08/742,805 filed Nov. 1, 1996, now abandoned, which is a continuation of copending commonly owned U.S. provisional application Ser. No. 60/022,180 filed Jul. 19, 1996, entitled DNA POLYMORPHISMS IN GENES THAT ARE USEFUL FOR TESTING AND SELECTING FOR INCREASED LITTER SIZE IN PIGS, priority is claimed under 35 U.S.C. Section 120.

GRANT REFERENCE

Work for this invention was funded in part by a grant from the United States Department of Agriculture, IAHEES/Hatch IOWO3148. The Government may have certain rights in this invention.

FIELD OF THE INVENTION

This invention relates generally to the detection of genetic differences for reproductive efficiency among pigs and particularly use of a genetic marker prolactin receptor gene which is indicative of the heritable trait of increased litter size.

BACKGROUND OF THE INVENTION

Reproductive efficiency, which can be defined as the number of pigs produced per breeding female, is the major limiting factor in the efficient production of pork. The number of pigs born alive in the U.S. averages approximately 9.5 pigs per litter. Heritability for litter size is low (10%–15%), and standard genetic methods of selecting breeding females on the basis of past litter size have not been effective. Therefore, there is a need for an approach that deals with selection for reproduction at the cellular or DNA level.

Chinese breeds are known for reaching puberty at an early age and for their large litter size. American breeds are known for their greater growth rates and leanness. Thus, it would be desirable to combine the best characteristics of both types of breeds, thereby improving the efficiency of U.S. pork production. These efforts would be greatly assisted by the discovery of genes or genetic markers that are associated with increased litter size in pigs.

RFLP analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science, Mar. 26–28, 1990*, incorporated herein by reference, reports on the polymorphism of swine major histocompatibility complex (MHC) genes for Chinese pigs, also demonstrated by RFLP analysis. Jung et al. *Animal Genetics*, 26:79–91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

Further, U.S. Pat. No. 5,550,024 to Rothschild et. al. discloses a polymorphism in the pig estrogen receptor gene which is associated with larger litter size, the disclosure of which is incorporated herein by reference.

Another pig hormone related to reproductive success is Prolactin. Prolactin (PRL) is an anterior pituitary peptide hormone involved in many different endocrine activities, but is essential for reproductive success. One of its best characterized functions is regulating milk production in adult mammals. PRL is required for the stimulation of lactogenesis, or synthesis of milk proteins. This action is mediated by its receptor (PRLR). PRLR belongs to the cytokine/GHR/PRLR superfamily. When activated by PRL, PRLR begins a signal transduction pathway, which ultimately activates transcription of genes such as β-casein and α-lactalbumin. When activated by PRL, PRLR begins a signal transduction pathway thought to involve the tyrosine kinase Jak2. Mutations in the carboxy-terminal end of the protein which change a specific phosphotyrosine residue prevents the receptor from activating Jak2 and ultimately interferes with the activation of transcription of the β-casein gene (Lebrun). Long and short forms of the receptor protein, as well as various transcript sizes have been characterized in the rat, mouse, rabbit, and human. (Boutin, Edery, Lesueur). However, it has been demonstrated that the short form is not capable of activating transcription of the milk protein genes. The mRNAs seen thus far originate from the same primary transcript and are due to alternative splicing, specifically in the untranslated regions in the rabbit and human. Recently, PRL has also been shown to stimulate the production of progesterone, required for maintenance of pregnancy, in large porcine luteal cells in vitro. PRLR is thought to mediate the effects of growth hormone (bST) injections on higher milk yield in cattle, and thus may be important in varying milk yield in pigs. In humans and mice, the growth hormone receptor (GHR) and PRLR map close together (Arden et al., 1990; Barker et al., 1992), making it likely that these two genes are linked in pigs. GHR has been mapped in pigs to chromosome 16, while PRLR is unmapped and no genetic variability has been reported for PRLR.

The present invention provides a genetic marker, based upon the discovery of polymorphisms in the prolactin receptor gene, which relates to increased average litter size in pigs. This will permit genetic typing of pigs for their prolactin receptor genes and for determination of the relationship of specific RFLPs to increased litter size. It will also permit the identification of individual males and females that carry the gene for larger litters. In the case of females it would permit that a female would be expected to produce a litter size larger than the average for their breed, or in the case of males for their female offspring to have larger litters than the breed average. Thus, the markers will be selection tools in breeding programs to develop lines and breeds that produce litters containing a larger number of offspring.

It is an object of the invention to provide a method of screening pigs to determine those more likely to produce larger litters.

Another object of the invention is to provide a method for identifying genetic markers for pig litter size.

A further object of the invention is to provide genetic markers for pig litter size.

Yet another object of the invention is to provide a kit for evaluating a sample of pig DNA for specific genetic markers of litter size.

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

SUMMARY OF THE INVENTION

To achieve the objects and in accordance with the purpose of the invention, as embodied and broadly described herein, the present invention provides a method for screening pigs to determine those more likely to produce a larger litter when bred or to select against pigs which have alleles indicating smaller litter sizes. As used herein "larger litters" means a significant increase in litter size above the mean of a given population. Thus, the present invention provides a method for screening pigs to determine those more likely to produce larger litters, and/or those less likely to produce larger litters, which method comprises the steps 1) obtaining a sample of genomic DNA from a pig; and 2) analyzing the genomic DNA obtained in 1) to determine which prolactin allele(s) is/are present. Briefly, a sample of genetic material is obtained from a pig, and the sample is analyzed to determine the presence or absence of a polymorphism in the prolactin receptor gene that is correlated with increased litter size.

As is well known to those of skill in the art, a variety of techniques may be utilized when comparing nucleic acid molecules for sequence differences. These include by way of example, restriction fragment length polymorphism analysis, heteroduplex analysis, single strand conformation polymorphism analysis, denaturing gradient electrophoresis and temperature gradient electrophoresis.

In a preferred embodiment the polymorphism is a restriction fragment length polymorphism and the assay comprises identifying the pig prolactin receptor gene from isolated pig genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from a pig prolactin receptor gene that is either known to have or not to have the desired marker. If a pig tests positive for the marker, such pig can be considered for inclusion in the breeding program. If the pig does not test positive for the marker genotype the pig can be culled from the group and otherwise used.

In a most preferred embodiment the gene is isolated by the use of primers and DNA polymerase to amplify a specific region of the gene which contains the polymorphism. Next the amplified region is digested with a restriction enzyme and fragments are again separated. Visualization of the RFLP pattern is by simple staining of the fragments, or by labeling the primers or the nucleoside triphosphates used in amplification.

In another embodiment, the invention comprises a method for identifying a genetic marker for pig litter size in a particular population. Male and female pigs of the same breed or breed cross or similar genetic lineage are bred, and the number of offspring produced by each female pig is determined. A polymorphism in the prolactin receptor gene of each pig is identified and associated with the number of offspring. Preferably, RFLP analysis is used to determine the polymorphism.

It is also possible to establish linkage between specific alleles of alternative DNA markers and alleles of DNA markers known to be associated with a particular gene (e.g. the prolactin receptor gene discussed herein), which have previously been shown to be associated with a particular trait. Thus, in the present situation, taking the prolactin receptor gene, it would be possible, at least in the short term, to select for pigs likely to produce larger litters, or alternatively against pigs likely to produce smaller litters, indirectly, by selecting for certain alleles of a prolactin receptor associated marker through the selection of specific alleles of alternative chromosome 16 markers. Examples of such markers known to be linked to prolactin receptor on porcine chromosome 16 includes SW1305, S0077, S0006, SW2411, SW1035 and S0111, which markers are all microsatellites and Growth Hormone Receptor (GHR). As used herein the term "genetic marker" shall include not only the polymorphism disclosed by any means of assaying for the protein changes associated with the polymorphism, be they linked markers, use of microsatellites, or even other means of assaying for the causative protein changes indicated by the marker and the use of the same to influence the litter size of an animal.

As used herein, the designation of a particular polymorphism is made by the name of a particular restriction enzyme. This is not intended to imply that the only way that the site can be identified is by the use of that restriction enzyme. There are numerous databases and resources available to those of skill in the art to identify other restriction enzymes which can be used to identify a particular polymorphism, for example http://darwin.bio.geneseo.edu which can give restriction enzymes upon analysis of a sequence and the polymorphism to be identified. In fact as disclosed in the teachings herein there are numerous ways of identifying a particular polymorphism or allele with alternate methods which may not even include a restriction enzyme, but which assay for the same genetic or proteomic alternative form.

Further due to the highly conserved nature of these genes it is expected that other animals will demonstrate polymorphism analogous to those disclosed herein, whether by sequence homology or similar protein affects. These are intended to be within the scope of the invention and included in the term "genetic marker".

The invention further comprises a kit for evaluating a sample of pig DNA for the presence in pig genetic material of a desired genetic marker located in the pig prolactin receptor gene indicative of the inheritable trait of large litter size. At a minimum, the kit is a container with one or more reagents that identify a polymorphism in the pig prolactin receptor gene. Preferably, the reagent is a set of oligonucleotide primers capable of amplifying a fragment of the pig prolactin receptor gene that contains the polymorphism. Preferably, the kit further contains a restriction enzyme that cleaves the pig prolactin receptor gene in at least one place.

The accompanying figures, which are incorporated herein and which constitute a part of this specification, illustrates one embodiment of the invention and, together with the description, serve to explain the principles of the invention.

DESCRIPTION OF THE FIGURES

FIG. 1 depicts the sequence of the 3' coding and untranslated region of the pig prolactin receptor gene (SEQ ID NO:3). The pig PCR fragment produced from the rabbit/human primers was purified using Amicon Microcon Filters as directed (Amicon, Inc.). Sequencing was done by the Iowa State University DNA Sequencing and Synthesis Facility. Region in italics represents ambiguity in sequence and may be ccaaaactac (SEQ ID NO:3) →Pig PCR primers.— Rabbit/human sequence.

FIG. 2 depicts the Polymorphic pattern of AluI digested PCR product. The forward primer 5'-CCC AAA ACA GCA GGA GAA CG-3' (SEQ ID NO:1) and the reverse primer 5'-GGC AAG TGG TTG AAA ATG GA-3' (SEQ ID NO:2) were used in the following PCR conditions: 93° C. for 3 minutes, and 35 cycles of 93° C. 30 seconds, 60° C. 1 minute, 70° C. 1 minute, and a final 72° C. 3 minutes. The Taq Polymerase was added last while samples were held at 80° C. PCR products were cut with Alu I (New England Biolabs) and separated on a 6% NuSieve (FMC) agarose gel at 120 volts for 4 hours at room temperature. Gels were stained with ethidium bromide. Lane 1 is 1-kb ladder, lanes 2–4 are the three different genotypes.

FIG. 5 illustrates the sequence (SEQ ID NO:14) surrounding the HinFI site in the intron between exons 8 and 9. Original primers are underlined. Each of the SNP locations are bolded. Additional primer sites designed for analysis are indicated with a line above and below the primers.

FIG. 6 is a chart depicting the expected band sizes for the HinFI test protocol.

FIG. 9 depicts sequence of porcine introns 3 and 4 and exon 4 which may be used to design alternate primers for the AluI site (SEQ ID NO:15). Exon 4 is bolded, intron 3 precedes the bolded segment and intron 4 follows. Also shown is human exon 4 (SEQ ID NO:16) and an alignment between human (SEQ ID NO:16) and porcine (SEQ ID NO:17) sequences together with porcine sequence for the introns flanking exon 4. This information helps to design alternate primers for these polymorphisms.

DETAILED DESCRIPTION OF THE INVENTION

Figure 3:
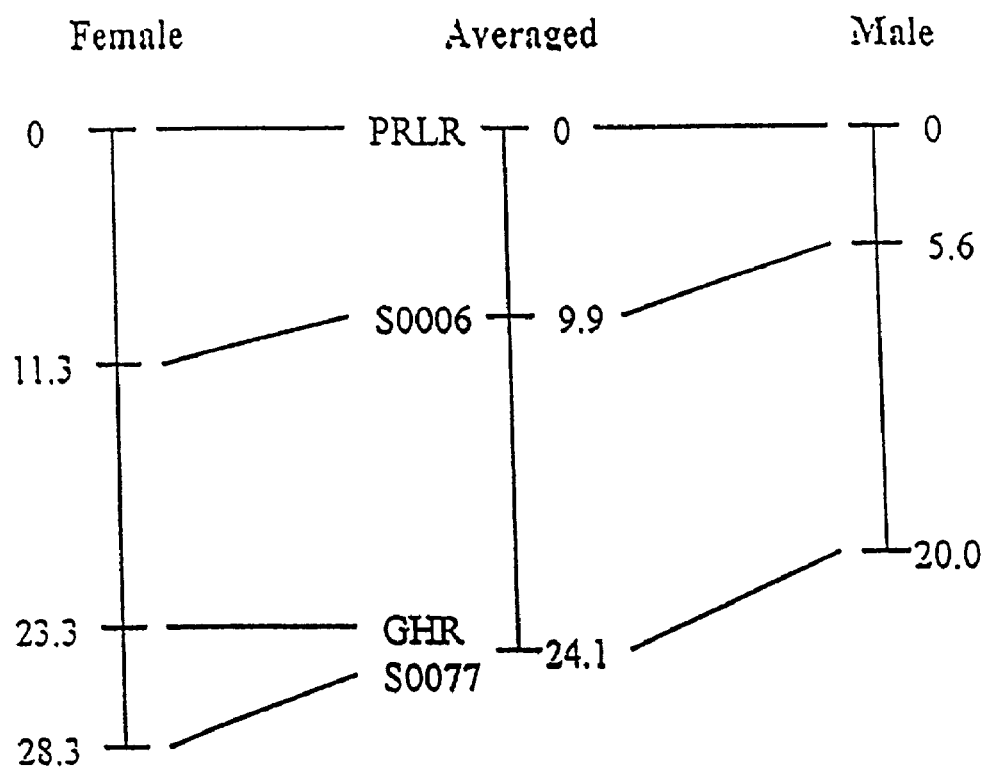
FIG. 3 depicts the position of PRLR in pig chr 16. Multiple point linkage was done using CriMap to produce a sex-averaged best-map with a LOD score of 3 or greater being considered as significant.

Reference will now be made in detail to the presently referred embodiments of the invention, which together with the following examples, serve to explain the principles of the invention.

The invention relates to genetic markers for litter size in pigs. It provides a method of screening pigs to determine those more likely to produce a larger litter when bred by identifying the presence or absence of a polymorphism in the prolactin receptor gene that is correlated with increased litter size.

Thus, the invention relates to genetic markers and methods of identifying those markers in a pig of a particular breed, strain, population, or group, whereby the female pig is more likely to produce a litter that is significantly increased in size (number) above the mean litter size for that particular breed, strain, population, or group. Any method of identifying the presence or absence of this marker may be used, including for example single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, micro-array-type detection of the prolactin gene, or other linked sequences of the prolactin receptor gene and examination for the markers in the 3' translated and non-translated region. Also within the scope of the invention includes assaying for protein conformational or sequences changes which occur in the presence of this polymorphism. The polymorphism may or may not be the causative mutation but will be indicative of the presence of this change and one may assay for the genetic or protein bases for the phenotypic difference.

The following is a general overview of techniques which can be used to assay for the polymorphisms of the invention.

In the present invention, a sample of genetic material is obtained from a pig. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, DNA Fingerprinting, An Introduction, W.H. Freeman & Co. N.Y. (1992). Genomic DNA can also be isolated from cultured primary or secondary cell cultures or from transformed cell lines derived from any of the aforementioned tissue samples.

Samples of animal RNA can also be used. RNA can be isolated from tissues expressing the prolactin receptor gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., Hum. Genet. 85:655–658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 μl) in a buffer of 50 mM Tris-HCl (pH 8.3), 50 mM KCl 1.5 mM $MgCl_2$, 0.5% Tween 20, 0.5% NP40 supplemented with 100 μg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten μl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in PCR Technology, Ehrlich, H.A. (ed.), Stockton Press, N.Y., which is incorporated herein by reference. PCR can be employed to amplify target regions in very small numbers of cells (1000–5000) derived from individual colonies from bone marrow and peripheral blood cultures. The cells in the sample are suspended in 20 μl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 μl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., Nucleic Acids Res. 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty μl of a 20 mg/ml solution of proteinase K and 150 μl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 μl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63–67; and Radding, 1982, Ann. Rev. Genetics 16:405–436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (CDNA) sequence from the RNA template are reverse transcriptase (RT), such as avian myeloblastosis virus RT, Moloney murine leukemia virus RT, or Thermus thermophilus (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, E. coli DNA polymerase I or its Klenow fragment, T4 DNA polymerase, Tth polymerase, and Taq polymerase, a heat-stable DNA polymerase isolated from Thermus aquaticus and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, Nucleic Acid Res. 17:12427–2448 (1989).

Allele Specific Oligonucleotide Screening Methods

Further diagnostic screening methods employ the allele-specific oligonucleotide (ASO) screening methods, as described by Saiki et al., Nature 324:163–166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Target regions of a test subject's DNA can be compared with target regions in unaffected and affected family members by ligase-mediated allele detection. See Landegren et al., Science 241:107–1080 (1988). Ligase may also be used to detect point mutations in the ligation amplification reaction described in Wu et al., Genomics 4:560–569 (1989). The ligation amplification reaction (LAR) utilizes amplification of specific DNA sequence using sequential rounds of template dependent ligation as described in Wu, supra, and Barany, Proc. Nat. Acad. Sci. 88:189–193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_m$). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W.H. Freeman and Co., N.Y. (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501–527 (1986), and Myers et al., in Genomic Analysis, A Practical Approach, K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE)

uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at the prolactin receptor locus can be differentiated using single-strand conformation polymorphism analysis, which identifies base differences by alteration in electrophoretic migration of single stranded PCR products, as described in Orita et al., Proc. Nat. Acad. Sci. 85:2766–2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., Am. J. Hum. Genet. 48:212–222 (1991). In another method, differences between target sequences can be detected by enzymatic cleavage of mismatched base pairs, as described in Nelson et al., Nature Genetics 4:11–18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with prolactin receptor polymorphisms.

Non-gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology at www.twt.com.

Non-PCR Based DNA Diagnostics

The identification of a DNA sequence linked to prolactin receptor can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and e, e', 5, 5'-5354amethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the porcine chromosome where prolactin receptor resides, and thus defining a genetic marker linked to prolactin receptor, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Additional enzymes, constructed probes and primers can be determined through routine experimentation, combined with the teachings provided and incorporated herein.

Genetic markers for pig litter size are determined as follows. Male and female pigs of the same breed or breed cross or derived from similar genetic lineages are mated. The number of offspring produced by each female pig is determined. RFLP analysis of the parental DNA is conducted as discussed above in order to determine polymorphisms in the prolactin receptor gene of each pig. The polymorphisms are associated with the number of offspring.

At least 20 and preferably at least 400 female pigs are used in making these determinations. The number of times each female produces a litter (i.e., the parity) is at least 1 time. Preferably, the cycle of breeding and giving birth is repeated at least 2 times and most preferably 3 times.

According to the invention, 4 polymorphisms in the prolactin receptor gene have been identified which have an association with litter size. The presence or absence of the markers, in one embodiment may be assayed by PCR RFLP analysis using the restriction endonuclease AluI, HinFI, MseI, or HpyCH4IV and amplification primers may be designed using analogous human or rabbit or other known prolactin sequences due to the high homology in the region surrounding the polymorphisms, or may be designed using known pig prolactin gene sequence data as exemplified in FIG. 1 or even designed from sequences obtained from linkage data from closely surrounding genes based upon the teachings and references herein. The sequences surrounding the polymorphism will facilitate the development of alternate PCR tests in which a primer of about 4–30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. According to the invention for the Alu I site a set of primers have been selected which amplify a 457 base pair fragment (forward primer 5'-CCC AAA ACA GCA GGA GAA CG-3' (SEQ ID NO:1) and the reverse primer 5'-GGC AAG TGG TTG AAA ATG GA-3' (SEQ ID NO:2)) after restriction polymorphic fragments of approximately 124, 110, 79, 77, and 67 base pairs are generated. The polymorphic site is located in the 110 base pair fragment. When the polymorphic cut site is present a 90 base pair fragment is produced. The polymorphic fragments were shown to be alleles, and each was shown to be associated with increased litter size for various breeds. Thus a pig which is heterozygous for the AluI fragment will exhibit a pattern of 124, 110, 90, 79, 77 and 67. A homozygote for the polymorphic cut site will exhibit a pattern of 124, 90, 79,77,67, while the other homozygote exhibits a pattern of 124,110, 79,77,67. The genotype associated with larger litter size alternates for different breeds. This outcome is similar to the situation disclosed in U.S. Pat. No.5,374,523 entitled "Allelic variants of Bovine Somatotropin gene: Genetic marker for Superior Milk Production in Bovine" where the inventor found an allelic polymorphism is the somatotropin gene and one allelic form was beneficial for Jersey cows and the alternate form was beneficial for Holstein cows.

For the HinFI site, a set of primers were designed, 5'-CAA GGT GGG AAC ATG AGT-3' SEQ ID NO:8 and 5'-AAT CCT TTT ATT TTT GGC CC-3' SEQ ID NO:9 with the use of HinFI which identifies an allele associated with increased litter size.

Another alternate gene form was identified by the inventors which is correlated with litter size and number born alive which is identifiable by a HpyCH4IV digestion. Primers were also identified to optimize a PCR based assay, 5'-GAT TAT TGT CTG GGC AGT GG-3' SEQ ID NO:10 and 5'-AAT CCT TTT ATT TTT GGC CC-3' SEQ ID NO:11.

Yet another alternate gene form was found which is similarly correlated with litter size and is identifiable in one embodiment by a Mse I restriction digestion. Primers were designed for optimizing of this assay: 5'-GAT TAT TGT CTG GGC AGT GG-3' SEQ ID NO:12 and 5'-CTA TTT CAC AAA AAC TGC GCT AC-3' SEQ ID NO:13.

Finally data is disclosed which observes the combinations of these alleles to help in screening for multiple markers.

The reagents suitable for applying the methods of the invention may be packaged into convenient kits. The kits provide the necessary materials, packaged into suitable containers. At a minimum, the kit contains a reagent that identifies a polymorphism in the pig prolactin receptor gene that is associated with an increased litter size. Preferably, the reagent is a PCR set (a set of primers, DNA polymerase and 4 nucleoside triphosphates) that hybridize with the pig prolactin receptor gene or a fragment thereof. Preferably, the PCR set and a restriction enzyme that cleaves the pig prolactin receptor gene in at least one place are included in the kit. Preferably, the kit further comprises additional means, such as reagents, for detecting or measuring the detectable entity or providing a control. Other reagents used for hybridization, prehybridization, DNA extraction, visualization etc. may also be included, if desired.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the prolactin receptor gene is present. Preferably, RFLP analysis is performed with respect to the pig prolactin receptor gene, and the results are compared with a control. The control is the result of a RFLP analysis of the pig prolactin receptor gene of a different pig where the polymorphism of the pig prolactin receptor gene is known. Similarly, the prolactin receptor genotype of a pig may be determined by obtaining a sample of its genomic DNA, conducting RFLP analysis of the prolactin receptor gene in the DNA, and comparing the results with a control. Again, the control is the result of RFLP analysis of the prolactin receptor gene of a different pig. The results genetically type the pig by specifying the polymorphism in its prolactin receptor genes. Finally, genetic differences among pigs can be detected by obtaining samples of the genomic DNA from at least two pigs, identifying the presence or absence of a polymorphism in the prolactin receptor gene, and comparing the results.

These assays are useful for identifying the genetic markers relating to litter size, as discussed above, for identifying other polymorphisms in the prolactin receptor gene that may be correlated with other characteristics, and for the general scientific analysis of pig genotypes and phenotypes.

The genetic markers, methods, and kits of the invention are also useful in a breeding program to improve litter size in a breed, line, or population of pigs. Continuous selection and breeding of sows that are at least heterozygous and preferably homozygous for a polymorphism associated with increased litter size would lead to a breed, line, or population having higher numbers of offspring in each litter of the females of this breed or line. Thus, the markers are selection tools.

The examples and methods herein disclose certain genes which have been identified to have a polymorphism which is associated either positively or negatively with a beneficial trait that will have an effect on litter size for females carrying this polymorphism. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism (allele). Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention.

One of skill in the art, once a polymorphism has been identified and a correlation to a particular trait established, will understand that there are many ways to genotype animals for this polymorphism. The design of such alternative tests merely represent optimization of parameters known to those of skill in the art and are intended to be within the scope of this invention as fully described herein.

EXAMPLE 1

Due to their high sequence homology and similarity in transcript processing, human (Boutin et al. 1989) and rabbit (Edery et al. 1989) cDNA sequences encoding the prolactin receptor were used to design degenerate primers overlapping the 3' coding and untranslated region. The primers amplified a fragment of approximately 500 base pairs in pig genomic DNA samples and human control. The forward primer 5'-TCA CAA GGT CAA C/TAA AGA TG-3' (SEQ ID NO:4) and the reverse primer 5'-TGG/A AGA AAG/A AGG CAA G/ATG GT-3' (SEQ ID NO:5)were used in the following PCR conditions: 93° C. for 3 minutes, 6 cycles of 93° C. 30 seconds, 47° C. 2 minutes, 72° C. 3 minutes, 36 cycles of 93° C. 30 seconds, 53° C. 2 minutes, 72° C. 5 minutes, and a final 72° C. 5 minutes. The Taq polymerase was added last while samples were held at 80° C.

Fragments from two animals were purified and sequenced in forward and reverse directions. The pig sequence from the coding region was translated to amino acids and compared with known sequences. A database search reported the rabbit and human PRLR sequences as the two best matches, with 82% and 74% positives respectively. From the pig DNA sequence, primers (forward primer 5'-CCC AAA ACA GCA GGA GAA CG-3' (SEQ ID NO:1) and the reverse primer 5'-GGC AAG TGG TTG AAA ATG GA-3' (SEQ ID NO:2)) were designed to amplify a 457 base pair fragment (FIG. 1). The restriction endonucleases Taq1, Sau3a, PvuII, MspI, and AluI, were used to digest the amplified product and a polymorphism was found with AluI. Resolution of the bands was obtained using agarose gel electrophoresis (FIG. 2). The fragment sizes of the PCR-RFLP were approximately 124, 110, 79, 77, and 67 base pairs with the polymorphic site being located in the 110 base pair fragment. When the polymorphic cut site was present a 90 base pair fragment was produced. See FIG. 4 for the fragment patterns produced. The PiGMaP reference families (Archibald et al. 1995) were genotyped, with all available families being informative. The genotypes were analyzed for 2-point linkage using CriMap software (Green et al. 1990), with LOD scores greater than 3 being significant. The PRLR locus was closely linked to three markers which are mapped to pig chromosome 16 of the published PiGMaP linkage map. A multiple point analysis was also done to produce a best chromosome 16 map (FIG. 3) involving all linked markers. Additional sequence of the porcine intron 3 and 4 and exon 4 is disclosed in FIG. 9.

EXAMPLE 2

PCR TEST for Prolactin Receptor Genetic Marker

The PCR amplification test was optimized with the following parameters.

Primers:

```
forward primer
5'-CCCAAAACAGCAGGAGAACG-3'        (SEQ ID NO:1)

reverse primer
5'-GGCAAGTGGTTGAAAATGGA-3'        (SEQ ID NO:2)
```

| PCR conditions: | |
|---|---|
| Cocktail Mix | 25 uL reaction |
| 10X PCR buffer (Promega) | 2.5 uL |
| 25 mM MgCl$_2$ (Promega) | 2.0 uL |
| 10 mM dNTP's (Boehringer Mannheim) | 0.5 uL |
| 20 pmol/uL forward primer | 0.5 uL |
| 20 pmol/uL reverse primer | 0.5 uL |
| dd Sterile H$_2$O | 17.5 uL |
| 12.5 ng/uL DNA | 1.5 uL |
| Taq Polymerase (Promega) | 0.125 uL |

The first six reagents should be mixed and 18.5uL of this pre-mix added to each reaction tube. Add the DNA next and then overlay with a drop of sterile mineral oil. Place the reaction tubes on the terminal cycler held at 80° C. Mix the Taq with the remaining cocktail and add 5uL to the reaction tubes, making sure to submerge the tip beneath the oil.

| Thermal Cycler Program: |
|---|
| 1. 93° C. 3 minutes |
| 2. 93° C. 30 seconds |
| 3. 60° C. 1 minute |
| 4. 72° C. 1 minute |
| 5. Return to step 2 for 34 cycles |
| 6. 72° C. 3 minutes |
| 7. 4° C. hold |

5 uL of the PCR product plus 2 uL of 6X loading dye should be placed on a 1% agarose gel to check. Run at 120V for 30 minutes and stain with Ethidium Bromide.

| AluI Digestion: | |
|---|---|
| Digestion Mix (per 20 uL PCR product) | Each |
| 10X NEBuffer 2 (New England Biolabs) | 2.5 uL |
| 8U/uL AluI (New England Biolabs) | 0.5 uL |
| dd Sterile H$_2$O | 2.0 uL |

Mix the reagents and add 5uL to each tube. Incubate the samples at 37° C. overnight.

Gel Electrophoresis:

The fragments are separated by loading the digest product plus 5uL 6X loading dye on a 6% NuSieve (FMC) agarose gel at 120 volts for 3 hours at room temperature. Stain gels with ethidium bromide. The fragment sizes of the PCR-RFLP are approximately 124, 110, 79, 77, and 67 base pairs with the polymorphic site being located in the 110 base pair fragment. When the polymorphic cut site is present a 90 base pair fragment is produced. Thus a heterozygote will have bands at 124,110,90,79,77 and 67. While homozygotes will have bands at 124,90,79,77 and 67 and 124,110,79, and 67 respectively.

Figure 4:
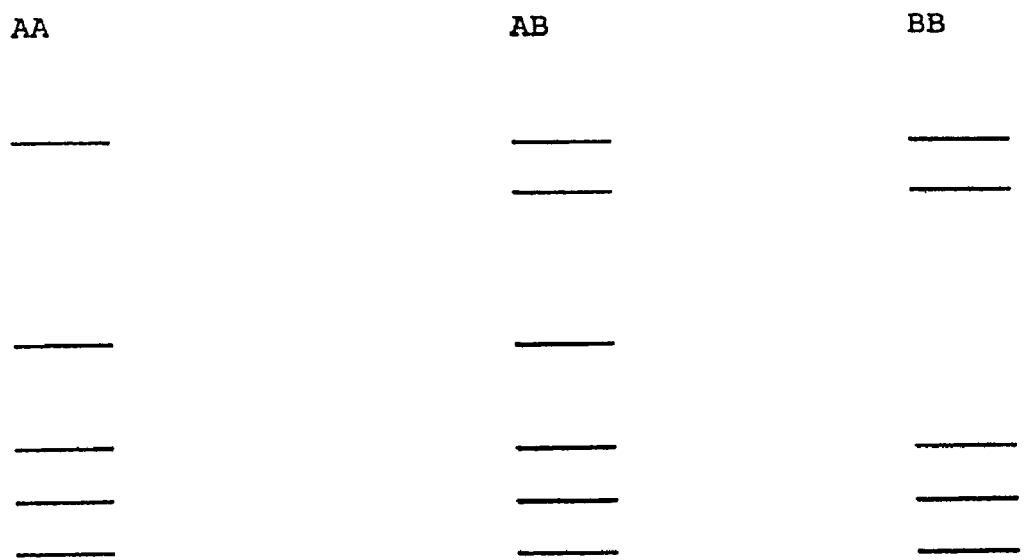
FIG. 4 is a diagram of the fragments obtained from the PCR test using PCR primers SEQ ID NOS: 1 and 2.
Figure 7:
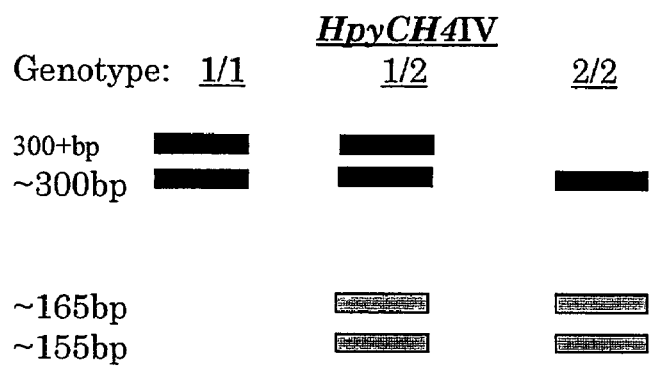
FIG. 7 is a chart depicting the expected band sizes of the HpyCH4IV test protocol.
Figure 8:
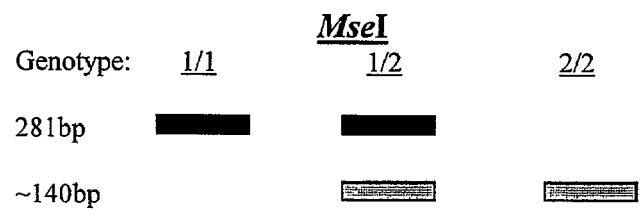
FIG. 8 is a chart depicting the band sizes expected for the MseI test protocol.

FIG. 4 is a diagram of the fragments obtained from the PCR test.(A is the allele with no AluI site, B is the allele having the AluI site).

EXAMPLE 3

Association Of Genotype With Litter Size

The PCR test was run as detailed in Example 2 on several sows from Pig Improvement Company, (PIC). The animals used were PIC line 19 sows which farrowed within a six month period and gilts which were born during this period that would be kept as breeding stock. Blood or tissue samples were collected and shipped to the laboratory where the DNA was extracted and used in the PRLR PCR test. Females had one to three records used in the analysis. Estimated Breeding Value for Total Number Born (BV TNB) was estimated using a mixed linear model where each successive parity of the sow is treated as a repeated record. Only the first three parities of a sow were used. The model includes the covariate of age at farrowing nested within parity, fixed effects of parity, service type (natural or AI), farm-month farrowed, and random permanent environmental and animal effects. Current $h^2$ is assumed as 0.10 and repeatability as 0.21. Average Number Born (AV NB) was calculated by taking the arithmetic mean of total parities (1–3) for each female.

Genotype comparisons were made for (BV TNB) and (AV NB) by averaging individual BV TNB and AV NB for each genotype. The results are seen in Table 1.

TABLE 1

| L19 Means for PRLR genotypes | | |
|---|---|---|
| | BV TNB | AV NB |
| BB Genotype (n = 18) | | |
| Mean | 0.2036 | 10.32 |
| Std Dev | 0.3984 | 1.746193 |
| Std Err | 0.0939 | 0.411838 |
| AB Genotype (n = 75) | | |
| Mean AB | 0.1203 | 9.66 |
| Std Dev AB | 0.5317 | 2.77238 |
| Std Err AB | 0.0622 | 0.320136 |
| AA Genotype (n = 109) | | |
| Mean AA | 0.0755 | 9.75 |
| Std Dev AA | 0.5757 | 2.513279 |
| Std Err AA | 0.0551 | 0.243064 |

EXAMPLE 4

Summary of Analyses of Prolactin Receptor With Large White Line and Landrace Based Lines and a Meishan Synthetic Line A total of 2,714 litter records from 1,077 sows were included in the litter size analyses. Traits included total number born (TNB) and number born alive (NBA) from five different PIC lines. The five lines examined were of Large White (two different origins) and Landrace origin, as well as synthetic lines consisting of ¾ Duroc, ¼ Large White, and Large White/Meishan origin. The PRLR genotype was shown to explain a statistically significant variation in litter size in three of the lines tested. Two of the lines did not show any statistically significant effect (P>0.1, results not shown). The least square means for TNB and NBA for each of the three statistically significant lines are summarized in Table 2.

DNA was extracted from blood and tail tissue. DNA was analyzed as described in Example 2 above.

Models contained fixed effects of: herd-season, service type, prolactin receptor, parity (1,2,3+)

covariable: ESR (estrogen receptor)

random effect: sire

Interactions among herd, ESR and prolactin receptor were tested for significance. Heritability for the litter traits was assumed as 0.10 and repeatability as 0.21. Allele substitution effects were estimated by substituting for PRLR genotype a covariate which included the number of A alleles present (0, 1, or 2). Dominance effects were estimated as the deviation of the heterozygote mean from the average of the homozygous genotype means.

Main Conclusions:

Large White synthetic

Indications of a dominance effect.

The sample consisted of 400 sows with 1197 litter records. AA animals have a 0.66 pig/litter advantage in Number Born Alive (NBA) over the other two genotypes (p<0.05). There are indications of a dominance effect with the B allele.

Meishan Synthetic

Significant dominance effect (over-dominance) -over all parities but mainly in first parity.

The sample consisted of 261 sows with 832 litter records. There is evidence of an additive effect for TNB (P<0.05) and NBA (P<0.05) and an overdominance effect for NBA in this line (<0.01).

Landrace Synthetic

Indications of an additive effect.

The sample consisted of 416 sows with 685 litter records. A greater than one pig per litter difference between the two homozygous genotypes was detected for both TNB (P<0.08) and NBA (P<0.1), with the A allele being favorable.

Effects on TNB showed the same trends as NBA for each of the populations. The results of Table 2 indicate that PRLR has a significant effect on litter size as measured by TNB and NBA in three commercial lines. It is apparent that the background genetics of each different line play a part in the manner and the magnitude that the trait is affected. In addition, significant differences were not found for average Birth Weight in any of the lines tested. This is a potentially valuable observation as there is normally an inverse relationship between litter size and average birth weight. The prolactin receptor allele may therefore provide a method of increasing the birth weight of larger litters.

TABLE 2

Least square means for each PRLR genotype across
all parities for TNB, NBA, and average birth weight
(ABW) for three commercial lines of pigs.

| Commercial Line | PRLR Genotype | TNB | NBA |
|---|---|---|---|
| Large White Synthetic | AA | 12.51 | 12.39 |
| | AB | 12.35 | 11.73 |
| | BB | 12.71 | 11.73 |
| | | | $P < 0.05$ |
| Effects | a | 0.10 | $-0.33^b$ |
| | d | $-0.26$ | $-0.33^a$ |
| Meishan Synthetic | AA | 13.64 | 12.94 |
| | AB | 14.35 | 13.74 |
| | BB | 13.96 | 13.27 |
| | | $P < 0.05$ | $P < 0.05$ |
| Effects | a | $0.16^b$ | $0.16^b$ |
| | d | $0.55^b$ | $0.63^c$ |
| Landrace Synthetic | AA | 12.13 | 11.33 |
| | AB | 11.72 | 10.92 |
| | BB | 10.98 | 10.31 |
| | | $P < 0.08$ | $P < 0.10$ |
| Effects | a | $051^b$ | $0.47^b$ |
| | d | 0.17 | 0.10 | a = additive effect; d = dominance effect; effects are significant at $^aP < 0.1$, $^bP < 0.05$, $^cP < 0.01$

EXAMPLE 5

Variation Among Different Breeds

In addition, samples from seven breeds have been typed, including the U.S. breeds Chester White, Duroc, Hampshire, Landrace, and Yorkshire; the Chinese Meishan; and the European Large White (Table 3).

TABLE 3

| | Genotype Frequencies | | | Allele Frequencies | |
|---|---|---|---|---|---|
| Breed | AA | AB | BB | A | B |
| Landrace n = 9 | .56 | .33 | .11 | .72 | .28 |
| Duroc n = 10 | .5 | .5 | 0 | .79 | .21 |
| Yorkshire n = 12 | 0 | .75 | .25 | .37 | .63 |
| Chester White n = 10 | .1 | .3 | .6 | .25 | .75 |
| Hampshire n = 11 | 0 | .09 | .91 | .05 | .95 |
| Meishan n = 9 | .33 | .44 | .22 | .56 | .44 |
| Large White n = 11 | .09 | .46 | .45 | .32 | .68 |

Some breed differences exist for gene frequencies at PRLR. The existence of a polymorphism located in the 3' region of the gene is interesting because PRLR alternative splicing is seen in this region of the gene in other species. The allele frequency differences among breeds suggest that one allele may have been selected for in some populations and against in others.

EXAMPLE 6

The region of the PLRL gene containing the polymorphic AluI site was amplified using primers PRLR-F4 (CGG CCG CAG AAT CCT GCT GC) SEQ ID NO:6 and PRLR-F5 (ACC CCA CCT TGT AAC CCA TCA TCC) SEQ ID NO:7 in a PCR containing 1x PCR Buffer 2 (Perkin Elmer), 2mM dATP, dTTP, dGTP and dCTP, 2.5mM $MgCl_2$, and 0.5 units AmpliTaq Gold (Perkin Elmer). Primers were used at a concentration of 5μM with a thermal cycling regime of 94° C. for 12 minutes followed by 30 cycles of 95° C. for 1 minutes, 60° C. for 1 minute and 72° C. for 1 minute and ending with a final step of 72° C. for 4 minutes. To each reaction 1.75μl of React 1 buffer (Life Technologies), 2.5 units of AluI and 8μl of $H_2O$ was added and incubation carried out at 37° C. for 2 hours. Following digestion 5μl of loading buffer was added and the products subject to electrophoresis on a 4% agarose gel composed of 3% NuSieve GTG agarose (FMC BioProducts) and 1% Seakem ME agarose (FMC BioProducts).

The region of the gene amplified contained one AluI site that was present in both of the PRLR alleles which acted as a positive control for digestion giving fragments of 127 and 35 base pairs in length. In the presence of the polymorphic AluI site the 127bp fragment is digested to fragments of 92 and 35 bp.

1) The test was used to genotype sows with breeding records from Landrace-based lines in a commercial nucleus herd. A total of 385 genotypes were obtained covering 711 litters.

Genotype I indicates no AluI site. Genotype 2 indicates presence of AluI polymorphism.

| Genotype | Sows | Litters | TNB | NBA |
|---|---|---|---|---|
| 11 | 149 | 274 | 11.23 | 10.85 |
| 12 | 173 | 309 | 11.24 | 10.77 |
| 22 | 63 | 128 | 10.42 | 9.89 |
| Additive affect | | | +0.41* | +0.48* |
| Dominant affect | | | +0.42+ | +0.4 |
| Significance: | + | $P < 0.10$ | * | $P < 0.05$ |

In this example, there is a significant effect on both TNB and NBA. The strongest significance is for an additive effect, although there is some indication of a dominant component. The breeder can now chose to select 11 and 12 animals for the production of subsequent generations to increase the reproductive potential of these lines and reestimating the size and type of effect in subsequent generations.

2) The test was used to genotype sows with breeding records from a new synthetic line of pigs maintained in a separate commercial nucleus herd. A total of 303 genotypes were obtained covering 536 litters.

| Genotype | Sows | Litters | TNB | NBA |
|---|---|---|---|---|
| 11 | 96 | 178 | 7.53 | 6.99 |
| 12 | 144 | 254 | 7.54 | 7.09 |
| 22 | 63 | 104 | 8.42 | 7.98 |
| Additive effect | | | +0.45+ | +0.50* |
| Dominant effect | | | +0.44 | +0.4 |
| Significance: | + | $P < 0.10$ | * | $P < 0.05$ |

In this example, there is a significant effect on both TNB and NBA. The strongest significance is for an additive effect, although there is some indication of a dominant component. The breeder can now chose to select 12 and 22 animals for the production of subsequent generations to increase the reproductive potential of these lines and reestimating the size and type of effect in subsequent generations.

3) The effect of PRLR genotype in lines selected for increased ovulation rate and embryonic survival was investigated.

Two selection lines and a control line were genotyped. Line 1 had undergone 16 generations of selection and Line 2, 8 generations of selection for traits related to reproduction. The control was maintained by random selection. Line 1 produced an average 6.1 more ova and 4.4 fully formed pigs than the control line, while Line 2 produced 2.2 more ova and 2.2 more fully formed pigs than the control line.

The frequency of PRLR genotype was determined for all 3 lines. The frequency of allele 2 was significantly higher in the selection lines. It was 0.33 higher in Line 1 compared with line C and 0.15 higher in Line 2 compared with the control (P<0.005).

Selection for PRLR allele 2 in these lines can be expected to lead to increases in ovulation rate and litter size (fully formed pigs).

| Allele | n | TNB |
|---|---|---|
| 11 | 76 | 10.09 |
| 12 | 542 | 10.43 |
| 22 | 392 | 10.81 |
| a | +0.36 | P < 0.21 |

EXAMPLE 7

Identification of Additional SNP Markers

1) Human PRLR sequence, GenBank accession numbers M31661, M60727 and AC025447 and AF091870 describing intron/exon boundaries were used to design primers for amplification from porcine DNA.

2) A PCR product of approximately 650 bp was amplified using a forward primer (5'GAT TAT TGT CTG GGC AGT GG 3') (SEQ ID NO:10) placed in exon 8 and a reverse primer (5'AAT CCT TTT ATT TTT GGC CC 3') SEQ ID NO:11) located in exon 9 of the prolactin receptor gene. These primers are indicated on the sequence. A 30 μl PCR reaction was prepared using 3 μl DNA, 1.5 mM MgC12, 0.2 mM each dNTP, 0.1 μM each primer, 1.5 U TaqGold Polymerase (Applied Biosystems, Foster City, Calif.) with 1× supplied reaction buffer. Thermal cycling conditions were denaturing at 94° C. for 12 min then 40 cycles of 94° C. for 1 min, 54° C. for 1 min and 72° C. for 1 min, following the cycling a final extension at 72° C. for 7 min occurred, then products were held at 4° C. until removal from the thermal cycler. PCR was performed in a Perkin Elmer 9700 thermal cycler (Applied Biosystems, Foster City, Calif.).

8.5 μl of PCR product was evaluated on a 2% agarose gel stained with ethidium bromide. PCR products were electrophoresed at 150 V for 30 min and then PCR product was visualized using ultraviolet light in an Alpha Imager (Alpha Innotech Corporation, San Leandro, Calif.).

10 μl of PCR product was prepared for sequencing. First, PCR product purification was performed using the QIAquick Spin columns (Qiagen Inc., Valencia, Calif.). The accompanying protocol for QIAquick PCR Purification Kit Protocol using a microcentrifuge was followed. Next cycle sequencing was performed using the ABI Prism BigDye Terminator v.3.0 Ready Reaction Sequencing Kit (Applied Biosystems, Foster City, Calif.). A 10 μl reaction was prepared using 4.0 μl of the Template Ready Reaction Mix, 3.0 μl of template (PCR purified template) and 3.2 pmol of primer. A separate reaction was prepared for both the forward and reverse primers (see above for primer sequence). Cycle sequencing thermal cycling conditions were 25 cycles of 96° C. for 10 sec, 50° C. for 5 sec and 60° C. for 4 minutes. Following cycling, products were held at 4° C. until ready for precipitation of product. The unincorporated BigDye terminators were removed using ethanol/sodium acetate precipitation. An 80 μl mix containing 3.0 μl 3M sodium acetate pH 4.6, 62.5 μl non-denatured, room temperature 95% ethanol and 14.5 μl deionized water was added to each of the cycle sequencing reactions. This was mixed well and incubated at room temperature for 15 minutes. Next samples were centrifuged for 20 min at 14,000 rpm. The supernatant was removed and pellets were washed with 250 μl 70% ethanol and then centrifuged for 5 min at 14,000 rpm. The supernatant was carefully and completely removed. Samples were then dried for 20 min at 60° C. to remove all ethanol residue. Samples were resuspended in 12 μl HiDi Formamide (Applied Biosystems, Foster City, Calif.). Samples were loaded onto the 3100 Genetic Analyzer (Applied Biosystems, Foster City, Calif.) and run using the standard sequencing default conditions.

3) The resulting sequence is as shown in FIG. 5.

Original primers are underlined. Each of the SNP locations are bolded and additional primer sites that were designed for SNP evaluation are indicated with a line above and below the primers. The dashes (---) indicate ambiguous DNA sequence.

The sequence was not available directly adjacent to each primer. In the middle of the product there is a polyA stretch of sequence from each direction whose length has not been determined. Protocols for the evaluation of each SNP individually follow. In order to create an RFLP site for the SNP located at position 523 a primer was designed to contain a non-complementary base in order to force a HinFI site.

PRLR-HinFI TEST PROTOCOL

PRLR(4)-F    5'CAA GGT GGG AAC ATG AGT 3'
             (SEQ ID NO:8)

PRLR-9R      5'AAT CCT TTT ATT TTT GGC CC 3'
             (SEQ ID NO:9)

| Method: | |
|---|---|
| 10x PCR Buffer II | 1.0 μl |
| 2 mM dNTP's | 1.0 μl |
| 25 mM MgCl₂ | 1.0 μl |
| PRLR(4)-F (5 μM) | 1.0 μl |
| PRLR-9R (5 μM) | 1.0 μl |
| Amplitaq Gold | 0.1 μl |
| QH₂O | 3.9 μl |
| Lysate | 1.0 μl |
| | 10.0 μl |

```
                94° C. 1 Min ⎫                    PE9700
94° C. 12 min → 54° C. 1 Min ⎬ × 40 →
                72° C. 1 Min ⎭

(9600 Ramp)    72° C. 7 min → 4° C. ∞
```

| Digestion: | |
|---|---|
| PCR Product | 10.0 μl |
| 10 × NE Buffer 2 | 1.3 μl |
| HinFI (10 U/μl) | 0.3 μl |
| Rediload | 0.5 μl |
| QH$_2$O | 0.9 μl |
| | 13.1 μl |

(37° C. 3 Hours)

Load and run on 4% 3:1 NuSieve Agarose at 150 volts for 35 min

PRLR-HpyCH4IV Test Protocol

```
PRLR-8F    5' GAT TAT TGT CTG GGC AGT GG 3'
           (SEQ ID NO:10)

PRLR-9R    5' AAT CCT TTT ATT TTT GGC CC 3'
           (SEQ ID NO:11)
```

| Method: | |
|---|---|
| 10 × PCR Buffer II | 1.0 μl |
| 2 mM dNTP's | 1.0 μl |
| 25 mM MgCl$_2$ | 0.6 μl |
| PRLR-8F (5 μM) | 0.2 μl |
| PRLR-9R (5 μM) | 0.2 μl |
| Amplitaq Gold | 0.1 μl |
| QH$_2$O | 5.9 μl |
| Lysate | 1.0 μl |
| | 10.0 μl |

```
                94° C. 1 Min ⎫                    PE9700
94° C. 12 min → 54° C. 1 Min ⎬ × 40 →
                72° C. 1 Min ⎭

(9600 Ramp)    72° C. 7 min → 4° C. ∞
```

Expected product size ~650 bp

| Digestion: | |
|---|---|
| PCR Product | 10.0 μl |
| 10 × NE Buffer 1 | 1.3 μl |
| HpyCH4IV (10 U/μl) | 0.4 μl |
| Rediload | 0.5 μl |
| QH$_2$O | 0.8 μl |
| | 14.0 μl |

(37° C. 3 Hours)

Load and run on 4% 3:1 NuSieve Agarose at 150 volts for 1 hr

PRLR-MseI TEST PROTOCOL

```
PRLR-8F
5' GAT TAT TGT CTG GGC AGT GG 3'
(SEQ ID NO:12)

PRLR(2-3)-R
5' CTA TTT CAC AAC TGC GCT AC 3'
(SEQ ID NO:13)
```

| Method: | |
|---|---|
| 10 × PCR Buffer II | 1.0 μl |
| 2 mM dNTP's | 1.0 μl |
| 25 mM MgCl$_2$ | 1.0 μl |
| PRLR-8F (5 μM) | 1.0 μl |
| PRLR(2-3)-R (5 μM) | 1.0 μl |
| Amplitaq Gold | 0.1 μl |
| QH$_2$O | 3.9 μl |
| Lysate | 1.0 μl |
| | 10.0 μl |

```
                94° C. 30 Sec ⎫                   PE9700
94° C. 12 min → 56° C. 30 Sec ⎬ × 35 →
                72° C. 30 Sec ⎭

(9600 Ramp)    72° C. 7 min → 4° C. ∞
```

| Digestion: | |
|---|---|
| PCR Product | 10.0 μl |
| 10 × NE Buffer 2 | 1.3 μl |
| MseI (10 U/μl) | 0.25 μl |
| 100 × BSA | 0.13 μl |
| Rediload | 0.5 μl |
| QH$_2$O | 0.82 μl |
| | 15.0 μl |

(37° C. 6 Hours)

Load and run on 4% 3:1 NuSieve Agarose at 150 volts for 30 min

Association Results

Introduction

Three SNPs in the pig PRLR gene were analyzed by PCR-RFLP. The markers are identified here using the restriction enzyme that reveals the polymorphism: M—Mse1, Hp—Hpych41V and Hin—HinFI. For all markers a 1 type allele indicates no restriction cut at the polymorphic site, a 2 indicates a cut.

The sample set consisted of sows from three different pure lines of pigs selected for maternal traits (referred to as dam lines in the industry). These lines consist of a Landrace based line (Line A), a Large White based line (Line B) and a synthetic line established by crossing Duroc and Large White lines (Line C). Litter size was determined by counting the number of piglets at birth: Total number born (TNB) is the sum of live and dead born piglets, Number born alive (NBA) is the number of live born piglets.

The number of sows with records that were genotyped and the allele frequencies per line are given here:

| | Line A | | Line B | | Line C | |
|---|---|---|---|---|---|---|
| SNP | No. sows | Freq. (2) | No. sows | Freq. (2) | No. sows | Freq. (2) |
| MseI | 231 | 0.82 | 190 | 0.90 | 320 | 0.63 |
| Hpych41V | 175 | 0.80 | 154 | 0.82 | 245 | 0.44 |
| HinFI | 197 | 0.12 | 174 | 0.06 | 307 | 0.32 |
| Haplotypes[#] | 121 | | 128 | | 128 | |
| 221 | | 0.82 | | 0.88 | | 0.37 |
| 211 | | 0.08 | | 0.09 | | 0.07 |
| 111 | | 0.00 | | 0.004 | | 0.21 |
| 212 | | 0.00 | | 0.007 | | 0.15 |
| 121 | | 0.06 | | 0.00 | | 0.05 |
| 112 | | 0.03 | | 0.007 | | 0.09 |
| 222 | | 0.00 | | 0.004 | | 0.05 |
| 122 | | 0.01 | | 0.00 | | 0.02 |

[#]:unambiguous allocation of haplotypes only. If MseI = 11, Hpych41v = 22, HinFI = 11 then haplotype = 121.

Analysis

Traits analyzed were: total numbers born (TNB) and numbers born alive (NBA).

Statistical model included the fixed effects of sow line (A, B, C), number of services (1, 2+), year-quarter of farrowing, cycle (1, 2, 3+), and the random effect of sire of the sow ($h^2=0.09$).

SNPs were included in the model as fixed effects and one SNP at a time. Additive effects were estimated as half the difference between the homozygotes and tested as a linear covariable (with SNP re-coded as having 0, 1 or 2 copies of allele 2). Dominance effects were estimated as the deviation of the heterozygote from the mean of the homozygotes and tested as a quadratic effect.

Two-way interactions between sow line and cycle with the SNP were tested for significance.

The cycle x SNP interaction was insignificant (P>0.3) across all markers.

The sow line x SNP interaction approached significance (P<0.2) for Mse1 (TNB). The interaction was significant (P<0.05) for Hpych41v (TNB and NBA). There was no sow line x SNP interaction for HinFI (P>0.5).

Haplotypes were assigned for animals where there was unambiguous allocation (i.e. sows were heterozygous for a maximum of one of the SNPs). For each haplotype, a variable was created with the scores 0, 1 or 2 if the animal had zero, one or two copies of the haplotype. Only line C was evaluated for the effect of haplotype as lines A and B were mainly of one haplotype. All the haplotypes were fitted in a single model as covariables and the least significant haplotype was removed sequentially until only haplotypes with P<0.20 remained. The LSMeans for these haplotypes were then estimated.

Results

In addition, to the within line analysis an across line analysis was conducted for M and Hin as there was no evidence for a significant interaction with line. This enables the data set to be increased thereby improving the estimate of any effects of marker genotype on litter size.

The results (across lines) indicate that there was a significant (P<0.05) effect of HinFI on TNB, and an indication of an effect of MseI on TNB. The effect appears to be additive for Hin with allele 2 being the preferred allele. Allele 2 is also preferred with snp M, although in this case the effect may have both additive and dominance components. The difference between the homozygous classes is between 0.61 (M) and (Hin) 0.8 pigs per litter. The effect is not statistically significant for NBA, however, the trend is in the same direction and the failure to reach significance may simply reflect the unequal genotype frequencies and the combination of lower mean values and higher standard errors for this trait in this dataset.

The results strongly support the existence of allelic variation in a gene influencing variation in litter size linked to PRLR. The MseI and HinFI markers can be used to select animals likely to have a greater breeding value for litter size. In particular, sows carrying allele 2 for these markers are preferred.

| | | | LSMeans (and s.e.) across lines | |
|---|---|---|---|---|
| | | | Traits | |
| SNP | Sig. | No. litters | TNB P < 0.20 | NBA P < 0.30 |
| MseI | | | | |
| | 11 | 149 | 9.88 (0.30)[a] | 9.01 (0.30) |
| | 12 | 425 | 10.42 (0.21)[ab] | 9.41 (0.21) |
| | 22 | 1011 | 10.49 (0.17)[b] | 9.50 (0.17) |
| | a | | +0.31+ | +0.25 |
| | d | | +0.24 | +0.16 |
| Hpych41v | Sig. | | sow line x SNP P < 0.05 | sow line x SNP P < 0.05 |
| | 11 | 250 | | |
| | 12 | 343 | | |
| | 22 | 644 | | |
| | a | | | |
| | d | | | |
| HinFI | Sig. | | P < 0.05 | P < 0.4 |
| | 11 | 992 | 10.37 (0.17)[b] | 9.47 (0.17) |
| | 12 | 361 | 10.82 (0.23)[a] | 9.65 (0.23) |
| | 22 | 99 | 11.17 (0.36)[a] | 9.95 (0.36) |
| | a | | +0.40** | +0.24 |
| | d | | +0.05 | −0.06 |

Columns with different superscripts differ (P < 0.05). Significance levels: +, P < 0.10; *, P < 0.05; , P < 0.01; *, P < 0.001

Data were also analyzed within lines for all SNP to see whether effects followed the same pattern across lines (and in the case of Hp as there was a significant effect of the line in the analysis).

Mse1: Additive effects had a positive sign for all SNPs for TNB and NBA as had been observed for the across line analysis. The additive effect was significant in line B. The dominance effect was significant in line A. The effect appears to be smaller in line C, however, in all cases genotype 11 has the lowest litters.

Hpych 41v: A significant interaction was found with sow line. Large dominance effects were seen for lines A and B (over-dominant in A, under-dominant in B). A slightly significant additive effect was observed in line C.

These results suggest that this marker may not be in linkage disequilibrium with the gene variants providing the phenotypic variation in these lines. However, it may be useful in some lines or situations where linkage disequilibrium is present between this marker and the (alleles) genes or mutations associated with variation in the trait.

HinFI: As for the across line analysis the additive effects are positive and they are significant in lines A and C. In the case of line B there are only two sows (with 3 litters) homozygous for allele 2, deleting these sows results in an additive effect that becomes large and positive. Based on the across line results and the Hin results for line A and C we anticipate that line B animals of genotype 22 will, on average, be expected to have larger litters than those of genotype 11 or 12. The two sows included here have below average litter size for this genotype by chance—as is expected for a trait such as litter size.

LSMeans (and s.e.) within lines for Mse1 (note s.e. values were the same for TNB and NBA)

| Line | Genotype | No. litters | Traits TNB | NBA |
|---|---|---|---|---|
| A | Sig. | | P < 0.20 | P < 0.30 |
| | 11 | 27 | 9.44 (0.67) | 8.54 |
| | 12 | 102 | 10.77 (0.45) | 9.73 |
| | 22 | 344 | 10.24 (0.33) | 9.39 |
| | a | | +0.40 | +0.43 |
| | d | | +0.93* | +0.77[+] |
| B | Sig. | | P < 0.10 | P < 0.10 |
| | 11 | 16 | 9.72 (0.82) | 9.06 |
| | 12 | 43 | 10.40 (0.53) | 9.22 |
| | 22 | 363 | 11.29 (0.27) | 10.18 |
| | a | | +0.79* | +0.56* |
| | d | | −0.11 | −0.46 |
| C | Sig. | | P < 0.80 | P < 1.0 |
| | 11 | 106 | 9.49 (0.40) | 8.59 |
| | 12 | 280 | 9.72 (0.30) | 8.75 |
| | 22 | 304 | 9.73 (0.31) | 8.70 |
| | a | | +0.12 | +0.06 |
| | d | | +0.11 | +0.11 |

LSMeans (and s.e.) within lines for Hpych4Iv

| Line | Genotype | No. litters | Traits TNB | NBA |
|---|---|---|---|---|
| A | Sig. | | P < 0.20 | P < 0.20 |
| | 11 | 24 | 9.45 (0.74)[ab] | 8.56 |
| | 12 | 106 | 10.57 (0.46)[b] | 9.66 |
| | 22 | 225 | 9.73 (0.40)[a] | 8.98 |
| | a | | +0.14 | +0.21 |
| | d | | +0.98 | +0.89[+] |
| B | Sig. | | P < 0.05 | P < 0.05 |
| | 11 | 38 | 11.79 (0.61)[a] | 10.45[a] |
| | 12 | 51 | 10.02 (0.51)[b] | 9.02[b] |
| | 22 | 264 | 11.49 (0.31)[a] | 10.29[a] |
| | a | | −0.15 | −0.08 |
| | d | | −1.62** | −1.35* |
| C | Sig. | | P < 0.30 | P < 0.60 |
| | 11 | 188 | 9.56 (0.37) | 8.78 |
| | 12 | 186 | 9.57 (0.36) | 8.48 |
| | 22 | 155 | 9.36 (0.38) | 8.44 |
| | a | | −0.10[+] | −0.17 |
| | d | | +0.11 | −0.13 |

LSMeans (and s.e.) within lines for HinFI

| Line | Genotype | No. litters | Traits TNB | NBA |
|---|---|---|---|---|
| A | Sig. | | P < 0.05 | P < 0.20 |
| | 11 | 321 | 9.89 (0.37)[a] | 9.15a |
| | 12 | 69 | 10.55 (0.52)[ab] | 9.55ab |
| | 22 | 12 | 12.37 (0.96)[a] | 11.04b |
| | a | | +1.24** | +0.95[+] |
| | d | | −0.58 | −0.55 |
| B | Sig. | | P < 0.50 | P < 0.70 |
| | 11 | 343 | 11.13 (0.28) | 10.04 |
| | 12 | 39 | 11.95 (0.62) | 10.48 |
| | 22 | 3 | 11.07 (1.86) | 9.08 |
| | a | | −0.03 | −0.48 |
| | d | | +0.85 | +0.92 |
| C | Sig. | | P < 0.30 | P < 0.70 |
| | 11 | 328 | 9.68 (0.30) | 8.82 |
| | 12 | 253 | 9.99 (0.31) | 8.87 |
| | 22 | 84 | 10.27 (0.43) | 9.17 |
| | a | | +0.30[+] | +0.18 |
| | d | | +0.02 | −0.13 |

It was also possible to analyze the effect of marker on litter size for Line C as the numbers of animals of the different haplotypes was greater in this line frequency table above). It can be seen that animals with haplotype 212 are found to have higher numbers of piglets and this effect is significant for HAP212 for TNB ($P<0.05$). This haplotype contains allele 2 for both M and Hin as might be expected from the individual marker results. However, it also suggests that a better result could be obtained by using both (or all three) markers in combination. This can be interpreted to show that whilst the markers are in strong linkage disequilibrium with the beneficial allele or mutation (that results in larger litters) there is not a perfect correlation; that is in most cases for either marker allele 2 is found together with the "big litter" gene, however, in a small number of cases this is not the case, here the chance that they are linked to the big litter gene is increased if both markers are allele 2.

Haplotype effects - only those where P < 0.20 are shown. Line C only. Haplotypes represent M.Hp.Hin genotypes.

| | | No. litters | Traits TNB | NBA |
|---|---|---|---|---|
| HAP212 Regression coefficient | | | +0.90 ± 0.32** | +0.57 ± 0.32[+] |
| LSMeans | 0 | 222 | 7.95 (1.20) | 6.99 |
| | 1 | 42 | 8.78 (1.32) | 7.35 |
| | 2 | 21 | 9.79 (1.14) | 8.29 |
| | Sig. | | P < 0.05 | P < 0.20 |
| HAP122 Regression coefficient | | | −1.51 ± 0.92[+] | −1.43 ± 0.92 |
| LSMeans | 0 | 275 | 9.89 (0.48) | 8.60 |
| | 1 | 9 | 7.93 (1.20) | 6.78 |
| | 2 | 1 | 8.70 (3.21) | 7.24 |
| | Sig. | | P < 0.20 | P < 0.30 |

LSMeans are for HAP212 and HAP122 evaluated together.

CONCLUSIONS

These examples show that additional markers can be identified in the PRLR gene that are in linkage disequilibrium with a gene(s) explaining variation in litter size in pigs. The results confirm those previously presented concerning the Alu1 polymorphism detected in the PRLR gene. It is also the case that any SNP from this region of pig chromosome 16 may be in linkage disequilibrium with the gene or genes. Those skilled in the art can generate snps from this region, conduct association studies as illustrated here, so as to determine which marker or combination of markers can be used to select for those animals likely to have a higher breeding value for litter size. That is those sows that will have larger litters or those sows and boars whose female progeny will have larger litters.

The following references are hereby incorporated in their entirety by reference:

Archibald, A., Haley, C., Brown, J., Couperwhite, S., McQueen, H., Nicholson, D., Coppieters, W., Van de Weghe, A., Stratil, A., Wintero, A., Fredholm, M., Larsen, N., Nielsen, V., Milan, D., Woloszyn, N., Robic, A., Dalens, M., Riquet, J., Gellin, J., Caritez, J. C., Burgaud, G., Ollivier, L., Bidanel, J. P., Vaiman, M., Renard, C., Geldermann, H., Davoli, R., Ruyter, D., Verstege, E., Groenen, M., Davies, W., Hoyheim, B., Keiserud, A., Andersson, L., Ellegren, H., Johansson, M., Marklund, L., Miller, J., Anderson Dear, D., Signer, E., Jeffreys, A., Moran, C., Le Tissier, P., Muladno., Rothschild, M., Tuggle, C., Vaske, D., Helm, J., Liu, H. C., Rahman, A., Yu, T. P., Larson, R. G., Schmitz, C. (1995) The PiGMaP Consortium Linkage Map of the Pig (Sus scofa). Mamm. Genome 6, 157–175.

Boutin, J., Edery, M., Shirota, M., Jolicoeur, C., LeSueur, L., Ali, S., Gould, D., Djiane, J., Kelly, P. (1989). Identification of cDNA Encoding a Long Form of Prolactin Receptor in Human Hepatoma and Breast Cancer Cells. Mol. Endocrinol. 3, 1455–1461.

Edery, M., Jolicoeur, C., Levi-Meyrueis, C., Dusanter-Fourt, I., Petridou, B., Boutin, J., LeSueur, L., Kelly, P., Djiane, J. (1989). Identification and Sequence Analysis of a Second From a Prolactin Receptor by Molecular Cloning of Complementary DNA From Rabbit Mammary Gland. Proc. Natl. Acad. Sci. USA 89, 2112–2116.

Green, P., Falls, K., Crooks S. (1990). Documentation for CRIMAP, version 2.4. Washington University School of Medicine, St. Louis.

Jammes, H., Schirar, A., Djiane, J. (1985) Differential Patterns in Luteal Prolactin and LH Receptors During Pregnancy in Sows and Ewes. J. Reprod. Fertil. 73, 27–35.

Kelly, P., Djiane, J., Postel-Vinay, M., Edery, M. (1991). The Prolactin/Growth Hormone Receptor Family. Endocrin. Rev. 12.235–251.

Lebrun, J., Ali, S., Groffin, V., Ullrich, A., Kelly, P. (1995). A Single Phosphotyrosine Residue of the Prolactin Receptor is Responsible for Activation of Gene Transcription. Proc. Natl. Acad. Sci. USA 92, 4031–4035.

LeSueur, L., Edery, M., Ali, S., Paly, J., Kelly, P. (1991). Comparison of Long and Short Forms of the Prolactin Receptor on Prolactin-Induced Milk Protein Gene Transcription. Proc. Natl. Acad. Sci. USA 88, 824–828.

Rothschild, M., Jacobson, C., Vaske, D., Tuggle, C., Wang, L., Short, T., Eckardt, G., Sasaki, S., Vincent, A., McLaren, D., Southwood, O., van der Steen, H., Mileham, A., Plastow, G. (1996). The Estrogen Receptor Locus is Associated With a Major Gene Influencing Litter Size in Pigs. Proc. Natl. Acad. Sci. 93, 201–205.

Rui, H., Djeu, J., Evans, G., Kelly, P., Farrar, W. (1992). Prolactin Receptor Triggering. J. Biol. Chem. 267, 24076–24081.

Yuan, W., Lucy, M. (1996). Effects of Growth Hormone, Prolactin, Insulin-Like Growth Factors, and Gonadotropins on Progesterone Secretion by Porcine Luteal Cells. J. Anim. Sci. 74, 866–872.

What is claimed is:

1. A method for identifying a genetic marker for litter size in animals comprising the steps of:
   breeding male and female animals of the same breed or breed cross or derived from similar genetic lineages;
   determining the number of offspring produced by each female animal;
   determining the polymorphism in the prolactin receptor gene as set forth in SEQ ID NO: 3 of each female animal; and
   associating the number of offspring produced by each female animal with said polymorphism thereby identifying a polymorphism for pig litter size.

2. The method of claim 1 further comprising the step of selecting animals for breeding which are predicted to have increased lifter size by said marker.

3. The method of claim 1 wherein said analysis comprises digestion of PCR amplified DNA with the restriction enzyme selected from the group consisting of AluI, HinFI and HypCH4IV.

4. A method for identifying a marker correlated with litter size comprising the steps of:
   obtaining a sample of genetic material from an animal, said sample comprising a prolactin receptor gene as set forth in SEQ ID NO: 3;
   assaying said prolactin receptor gene presented in said sample for a polymorphism;
   correlating whether a statistically significant association exists between said polymorphism and litter size in an animal of a particular breed, strain, population, or group whereby said animal can be characterized for said marker.

5. The method of claim 4 wherein said animal is a pig.

* * * * *

UNITED STATES PATENT AND TRADEMARK OFFICE
CERTIFICATE OF CORRECTION

PATENT NO. : 7,081,335 B2  
APPLICATION NO. : 09/900063  
DATED : July 25, 2006  
INVENTOR(S) : Rothschild et al.

It is certified that error appears in the above-identified patent and that said Letters Patent is hereby corrected as shown below:

Col. 1, lines 24-25:
DELETE:
After Agriculture, "IAHEES/Hatch IOWO3148"
ADD:
After Agriculture, --USDA/CSREES Grant Numbers 96-CRHF-0-6019 and 97-CRHF-0-6019--

Claim 2, Col. 37, line 39:
DELETE:
After increased "lifter"
ADD:
After increased --litter--

Signed and Sealed this

Fourteenth Day of November, 2006

JON W. DUDAS  
*Director of the United States Patent and Trademark Office*